United States Patent [19]

Humber et al.

[11] 4,346,090

[45] Aug. 24, 1982

[54] 13-CHLORO-BENZOCYCLOHEP-TAPYRIDOISOQUINOLINES AND USE AS NEUROLEPTICS

[75] Inventors: Leslie G. Humber, Dollard des Ormeaux; François T. Bruderlein, Guertin Montreal; André A. Asselin, St. Laurent, all of Canada

[73] Assignee: Ayerst, McKenna & Harrison Ltd., Montreal, Canada

[21] Appl. No.: 817,660

[22] Filed: Jul. 21, 1977

[51] Int. Cl.³ .................. A61K 31/435; C07D 221/18
[52] U.S. Cl. ........................................ 424/258; 546/42
[58] Field of Search ..................... 260/289 C; 424/258; 546/42

[56] References Cited

U.S. PATENT DOCUMENTS 3,852,452 12/1974 Bruderlein et al. ............. 260/289 C
3,861,751 1/1968 Humber ......................... 260/289 C

OTHER PUBLICATIONS

Humber et al., Abstract of Papers, 167th A C S M & G., Los Ang. Cal., 1974, Abstract MEOI-5.
Voith et al., Psychopharmacologia (Berl) 42, pp. 11–20 (1975).
Winthrop et al., J. Org.Chem., 27, p. 230 (1962).

*Primary Examiner*—David B. Springer
*Attorney, Agent, or Firm*—Adley F. Mandel

[57] ABSTRACT

13-Chloro-octahydrobanzo[6,7]cyclohepta[1,2,3-de]-pyrido[2,1-a]isoquinolin-5-ols, substituted on the piperidine ring with lower alkyl or a cycloalkyl are disclosed. The compounds are useful CNS depressants. Methods for their preparation and use also are disclosed.

8 Claims, No Drawings

13-CHLORO-BENZOCYCLOHEP-TAPYRIDOISOQUINOLINES AND USE AS NEUROLEPTICS

BACKGROUND OF THE INVENTION (a) Field of the Invention

The present invention relates to 13-chloro-benzocycloheptapyridoisoquinoline derivatives and to processes for preparing these compounds.

The 13-chloro-benzocycloheptapyridoisoquinoline derivatives of this invention possess valuable pharmacologic properties. For example, the compounds exhibit useful antipsychotic activity. More specifically, the 13-chloro-benzocycloheptapyridoisoquinoline derivatives are central nervous system depressant agents and, thus, are useful as neuroleptic drugs. In addition, the 13-chloro-benzocycloheptapyridoisoquinoline derivatives possess a low order of toxicity.

The combination of attributes stated above renders the 13-chloro-benzocycloheptapyridoisoquinolines of this invention useful and desirable as therapeutic agents for treating schizophrenia.

(b) Prior Art

U.S. Pat. No. 3,657,250, issued Apr. 18, 1972 and U.S. Pat. No. 3,852,452, issued Dec. 3, 1974 disclose benzocycloheptapyridoisoquinoline derivatives in which a carbon atom of the pentacyclic ring system bearing a hydroxyl or lower alkanoyloxy also bears a lower alkyl, lower alkenyl, lower alkynyl, phenyl or cycloalkyl containing 3–6 carbon atoms which may be optionally substituted with a lower alkyl. The present disclosure relates to 13-chloro-benzocycloheptapyridoisoquinoline. These new benzocycloheptapyridoisoquinoline derivatives differ from those in the prior art by having chloro substituent on an aromatic portion thereof.

SUMMARY OF THE INVENTION

The 13-chloro-benzocycloheptapyridoisoquinoline derivatives of the present invention are represented by formula 1

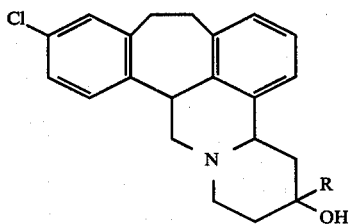

in which R is lower alkyl or cycloalkyl containing 3–6 carbon atoms.

The pharmaceutically acceptable acid addition salts are also included within the scope of this invention.

Included within the scope of this invention are the stereochemical isomers of the compounds of formula 1 which result from asymmetric centers, contained therein. These isomeric forms are purified readily by crystallization or chromatography.

Individual optical isomers of the compounds of formula 1, which might be separated by fractional crystallization of the diastereoisomeric salts formed thereof, for instance, with d- or l-tartaric acid or D-(+)-α-bromocampher sulfonic acid, are also included.

The preferred compound of formula 1 is represented by formula 1a

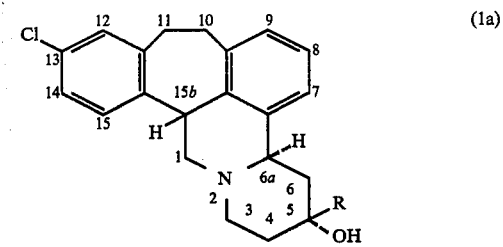

in which R is defined herein.

A preferred group of compounds of formula 1a are those in which R is lower alkyl.

Another aspect of this invention involves a method of producing neuroleptic effects in a mammal which comprises administering to said mammal an effective neuroleptic amount of a compound of formula 1, or a pharmaceutically acceptable salt thereof.

Still another aspect of this invention involves a pharmaceutical composition comprising a compound of formula 1, or a pharmaceutically acceptable salt thereof, and a pharmaceutically acceptable carrier.

DETAILS OF THE INVENTION

With reference to formula 1a the hydroxyl at position 5 is trans to the hydrogen atom in position 15b and cis to the hydrogen atom in position 6a.

Subsequent to the filing of the above-noted U.S. Pat. Nos. 3,657,250 and 3,852,452, the stereochemistry of the compounds described as isomer A and isomer B therein have been assigned on the basis of mechanistic, spectral and X-ray crystallography considerations. Accordingly, a compound of formula 1a in which the 6a-H is α corresponds to the isomer A disclosed in the Patent. (isomer B has similar stereochemistry except that the 6a-H is β).

The 13-chloro-benzocycloheptapyridoisoquinoline derivatives of this invention are capable of forming acid addition salts with pharmaceutically acceptable acids. The acid addition salts are prepared by reacting the base form of the 13-chloro-benzocycloheptapyridoisoquinoline derivatives with either one equivalent or preferably an excess of the appropriate acid in an organic solvent, such as ether or an ethanol-ether mixture. Such salts may advantageously be used for the purpose of isolating and/or purifying the compounds of this invention, and may be transformed in a manner known per se into the corresponding salts with pharmaceutically acceptable acids. These salts, when administered to mammals, exhibit the same pharmacologic activities as the corresponding bases. For many purposes it is preferable to administer the salts rather than the base compounds. Among the acid addition salts suitable for this purpose are salts such as the sulfate, phosphate, lactate, tartrate, maleate, citrate and hydrochloride. Both the base compounds and the above acid addition salts have the distinct advantage of possessing a relatively low order of toxicity.

The term "lower alkyl" as used herein contemplates straight chain alkyl radicals containing from one to six carbon atoms and branched chain alkyl radical containing up to four carbon atoms and includes methyl, ethyl, propyl, isopropyl, butyl, isobutyl, and t-butyl.

The useful neuroleptic activity of the 13-chloro-benzocycloheptapyridoisoquinoline derivatives of formulae 1 and 1a and their acid addition salts with pharmaceutically acceptable acids may be demonstrated in standard pharmacologic tests, such as, for example, the tests commonly used for detecting neuroleptic activity described by A. Randrup and L. Munkvad in "Amphetamines and Related Compounds", E. Costa and S. Garattini, Eds., Raven Press, New York, N.Y., 1970, pages 695–713. More specifically, by using the pharmacologic tests described by K. Voith and F. Herr in Psychopharmacologia, 42, 11-20 (1970), a preferred compound of this invention, (6a,15b-trans)-(5-hydroxyl,15b-H-trans)13-chloro-5-isopropyl-1,4,5,6,6a,10,11,15b-octahydro-5H-benzo[6,7]-cyclohepta[1,2,3-de]-pyrido[2,1-a]isoquinoline-5-ol (described in Example 8), exhibits potent neuroleptic activity. More explicitly, in the rat, neuroleptic acitivity is observed at a dose range of 0.05 to 1.3 mg/kg, i.p. of body weight.

This finding of potent neuroleptic activity of the latter compound is a surprising and unexpected result since other chloro derivatives of benzocycloheptapyridoisoquinoline do not exhibit neuroleptic activity at such low dose ranges. For example, in the test "d-Amphetamine-Induced Stereotyped Behavior in Rats", a test which illustrates neuroleptic activity, the above mentioned 13-chloro compound abolishes the amphetamine-induced sniffling, licking and gnawing at a minimal effective dose (i.p.) of 1.25 mg/kg of body weight. In contrast, the corresponding 9-chloro, 12-chloro and 14-chloro compounds require doses of 10, 20 and >20 mg/kg, i.p., respectively, to abolish the amphetamine-induced activity.

When the 13-chloro-benzocycloheptapyridoisoquinoline derivatives of this invention are used as neuroleptic agents in mammals, e.g. rats and mice, they are used alone or in combination with pharmacologically acceptable carriers, the proportion of which is determined by the solubility and chemical nature of the compound, chosen route of administration and standard biological practice. For example, they may be administered orally or parenterally by injection.

For administration to a mammal by parenteral injection, it is preferred to use the compounds of formula 1 in solution in a sterile aqueous vehicle which may also contain other solutes such as buffers or preservatives, as well as sufficient quantities of pharmaceutically acceptable salts or of glucose to make the solution isotonic.

When the compounds of this invention are employed as neuroleptic agents in mammals, orally effective, neuroleptic amounts of the compounds are administered to the mammal, either alone or combined with pharmaceutically acceptable excipients in a dosage form, i.e. capsule or tablet, or the compounds are administered orally in the form of solutions or suspensions.

The tablet compositions contain the active ingredient in admixture with non-toxic pharmaceutical excipients known to be suitable in the manufacture of tablets. Suitable pharmaceutical excipients are, for example, starch, milk sugar, certain types of clay and so forth. The tablets may be uncoated or they may be coated by known techniques so as to delay disintegration and absorption in the gastrointestinal tract and thereby provide a sustained action over a longer period.

The aqueous suspensions of the invention contain the active ingredient in admixture with one or more non-toxic pharmaceutical excipients known to be suitable in the manufacture of aqueous suspensions. Suitable excipients are, for example, methylcellulose, sodium alginate, gum acacia, lecithin and so forth. The aqueous suspensions may also contain one or more preservatives, one or more colouring agents, one or more flavouring agents and one or more sweetening agents.

Non-aqueous suspensions may be formulated by suspending the active ingredient in a vegetable oil, for example, arachis oil, olive oil, sesame oil, or coconut oil, or in a mineral oil, for example liquid paraffin, and the suspension may contain a thickening agent, for example beeswax, hard paraffin or cetyl alcohol. These compositions may also contain a sweetening agent, a flavouring agent and an anti-oxidant.

The dosage of the present therapeutic agents will vary with the form of administration and the particular compound chosen. Furthermore, it will vary with the particular host under treatment. Generally, treatment is initiated with small dosages substantially less than the optimum dose of the compound. Thereafter, the dosage is increased by small increments until the optimum effect under the circumstances is reached. In general, the compounds of this invention are most desirably administered for neuroleptic purposes at a concentration level that will generally afford effective results without causing any harmful or deleterious side effects for example, catalepsy, and preferably at a level that is in a range of from about 0.01 mg to about 100 mg per kilogram body weight per day, although as aforementioned variations will occur. However, a dosage level that is in the range of from about 0.1 mg to about 10 mg per kilogram body weight per day is most desirably employed in order to achieve effective results.

For the preparation of the 13-chloro-benzocycloheptapyridoisoquinoline derivatives of formula 1, the preferred starting material is the aminoketone of formula 2.

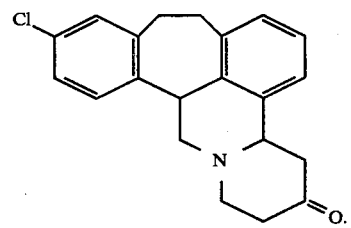

The aminoketone of formula 2 is converted to the compound of formula 1 by reacting the aminoketone with an appropriate Grignard reagent of formula R-(magnesium halide) in which R is as defined herein and the halide is chlorine, bromine or iodine in an inert solvent, for example, diethyl ether or tetrahydrofuran, according to the conditions of the Grignard reaction. In this manner the corresponding compound of formula 1 in which R is as defined herein is obtained. Suitable reaction times and temperatures range from 15 minutes to six hours and −40° to 90° C., respectively.

Alternatively, the aminoketone of formula 2 is reacted with an appropriate organolithium reagent of formula R-Li in which R is as defined herein under the same conditions described hereinbefore for the Grignard reaction. In this manner the corresponding compound of formula 1 in which R is as defined herein is obtained.

The following examples illustrate further this invention.

EXAMPLE 1

2-Chloro-10,11-dihydro-5H-dibenzo[a,d]cyclohepten-5-ylideneacetic Acid

Trimethylphosphonoacetate (0.53 mole) is added dropwise with stirring to a suspension of sodium hydride (0.48 mole, 50% dispersion in oil) in 250 ml of tetrahydrofuran at 30°–35° C. After the addition, the reaction is stirred for one hr at 20°–30° C. To this reaction mixture, 2-chloro-10,11-dihydro-5H-dibenzo[a,d]cyclohepten-5-one[0.16 mole, described by S. O. Winthrop, et al., J. Org. Chem., 27, 230 (1962)] in 400 ml of tetrahydrofuran is added. After refluxing for 20 hr the red colored solution is cooled to 0° to 5° C. and water is added dropwise. The aqueous solution is evaporated to remove most of the tetrahydrofuran and extracted with ethyl acetate. The organic phase is dried over magnesium sulfate and evaporated. The residue is subjected to chromatography on silica gel using benzene-hexane (1:1) and the eluates are evaporated to give 2-chloro-10,11-dihydro-5H-dibenzo-[a,d]cyclohepten-5-ylideneacetic acid ethyl ester. The latter compound (11.0 g) is dissolved in ethanol (110 ml) and the solution is added to 10% aqueous potassium hydroxide (110 ml). The resulting solution is refluxed for 3 hr. After the removal of the ethanol by evaporation, the aqueous phase is washed with diethyl ether, adjusted to pH 2 with conc. hydrochloric acid and extracted with chloroform. The chloroform extract is washed with water, dried over magnesium sulfate and evaporated. The residue is crystallized from diethyl ether-hexane to give the title compound as crystals, mp 155°–175° C.

EXAMPLE 2

2-Chloro-10,11-dihydro-5H-dibenzo[a,d]cyclohepten-5-ylacetic Acid

A solution of 2-chloro-10,11-dihydro-5H-dibenzo[a,d]-cyclohepten-5-ylideneacetic acid (23.5 g, described in Example 1) in ethanol (100 ml, hot) is added to 5% sodium amalgam (100 g). The mixture is stirred at 60°–70° C. for 3 hr and decanted. The solution is evaporated of half its original volume, acidified with conc. hydrochloric acid and extracted with chloroform. The organic extract is dried and evaporated. The residue is crystallized from diethyl ether-hexane to give the title compound as crystals, mp 142°–146° C.

EXAMPLE 3

2-Chloro-10,11-dihydro-5H-dibenzo[a,d]cyclohepten-5-ylacetyl Azide

To a magnetically stirred, ice cold solution of 2-chloro-10,11-dihydro-5H-dibenzo[a,d]cyclohepten-5-ylacetic acid (20.0 g, described in Example 2) in dry tetrahydrofuran (400 ml) is added, under an atmosphere of dry nitrogen, triethylamine (13 ml) and ethyl chloroformate (11.6 g). After stirring for 1 hr at 0° C., the suspension is cooled to −10° C. and a solution of sodium azide (6.4 g) in distilled water (40 ml) is added. After stirring for a further 1 hr at −10° C., the reaction mixture is diluted with diethyl ether (200 ml). The organic phase is dried over magnesium sulfate and evaporated to give the title compound.

EXAMPLE 4

2-Chloro-10,11-dihydro-5H-dibenzo[a,d]cyclohepten-5-ylmethylisocyanate

A solution of 2-chloro-10,11-dihydro-5H-dibenzo[a,d]cyclohepten-5-ylacetyl azide (2.6 g, described in Example 3) in benzene (30 ml) is heated at reflux for 1 hr. Vigorous evolution of nitrogen takes place. The toluene is removed under reduced pressure to yield the title compound as an oil, ir (film) 2250 cm$^{-1}$.

EXAMPLE 5

N-Formyl-2-chloro-10,11-dihydro-5H-dibenzo[a,d]cyclohepten-5-yl Methylamine

To a stirred suspension of sodium borohydride (10.0 g) in 100 ml of dimethoxyethane at 0° C. under nitrogen, a solution of 2-chloro-10,11-dihydro-5H-dibenzo[a,d]cyclohepten-5-ylmethylisocyanate (21.8 g, described in Example 4) in 200 ml of dimethoxyethane is added dropwise. The suspension is stirred for 20 hrs at 0° C. and concentrated under reduced pressure. Chloroform is added to the residue and the solution is cooled to 0° C. Hydrochloric acid (1 N) is added dropwise to destroy the complex and the organic extract is separated, dried and evaporated. The residue is subjected to chromatography on silica gel using 50% acetone in benzene and the eluate are evaporated. The residue is crystallized from diethyl ether-hexane to give the title compound as crystals, mp 122°–124° C.

EXAMPLE 6

10-Chloro-1,7,8,12b-tetrahydrobenzo[1,2]cyclohepta[3,4,5-de]isoquinoline

Polyphosphoric acid (50 g) is added to N-formyl-2-chloro-10,11-dihydro-5H-dibenzo[a,d]cyclohepten-5-yl methylamine (5.0 g, described in Example 5) and the mixture is stirred in an open flask at 150° C. for 3 hrs. The solution is poured into ice (500 g) and the precipitate is collected. The precipitate is partitioned between 10% aqueous sodium hydroxide and ethyl acetate (1:1). The organic phase is separated, dried over sodium sulfate and evaporated. The residue is subjected to chromatography on silica gel using acetone-benzene (1:5) and the eluates are evaporated. The residue is crystallized from diethyl ether to give the title compound as crystals, mp 106° C. The latter compound is dissolved in diethyl ether and anhydrous hydrogen chloride is bubbled into the solution. The precipitate is collected and crystallized from acetone to obtain the hydrochloride salt of the title compound, mp 200°–205° C.

EXAMPLE 7

(6a,15b-trans)-13-Chloro-1,3,4,6,6a,10,11,15b-octahydro-5H-benzo-[6,7]cyclohepta[1,2,3-de]pyrido[2,1-a]isoquinoline-5-one: 2

Freshly distilled methyl vinyl ketone (0.04 mole, stabilized with hydroquinone) is added to a suspension of 10-chloro-1,7,8,12b-tetrahydrobenzo[1,2]cyclohepta[3,4,5-de]isoquinoline as the hydrochloride salt (0.13 mole, described in Example 6) in toluene (50 ml) and dimethylformamide (17 ml). The mixture is heated at 100°–105° C. for 1.5 hrs. cooled to 25° C. and diethyl ether is added. The solid is collected and partitioned between ethyl acetate and 5% sodium bicarbonate solution. The organic phase is separated, dried and evaporated. The residue is subjected to chromatography on silica gel using chloroform-benzene (1:1). The appropriate eluate fractions are evaporated and the residue is triturated with diethyl ether to give the title compound, mp 178° C. (softening point). Other appropriate eluate fractions are evaporated and the residue is crystallized from ether to give the corresponding cis isomer, (6a,15b-cis)-13-chloro-1,3,4,6,6a,10,11,15b-octahydro-5H-benzo-[6,7]cyclohepta[1,2,3-de]pyrido[2,1-a]isoquinolin-5-one, having a mp 200°–205° C.

EXAMPLE 8

(6a,15b-trans)-(5-hydroxyl,15b-H-trans)-13-Chloro-5-isopropyl-1,4,5,6,6a,10,11,15b-octahydro-5H-benzo[6,7-]cyclohepta[1,2,3-de]pyrido[2,1-a]isoquinoline-5-ol; 1a (R=isoproyl)

To magnesium turnings (1.8 g) in diethyl ether (10 ml) activated with a few crystals of iodine is added dropwise isopropyl chloride (5.8 g, 0.074 mole) in diethyl ether (50 ml) in such a way that a gentle reflux is maintained (about 1 hr) to obtain the Grignard reagent, isopropyl magnesium chloride. The Grignard reagent is then stirred for 1 hr at room temperature, diluted with more ether (50 ml), cooled to −20° C. and added to (6a,15b-trans)-13-chloro-1,3,4,6,6a,10,11,15b-octahydro-5H-benzo[6,7]cyclohepta[1,2,3-de]pyrido[2,1-a]isoquinolin-5-one (2.5 g, described in Example 7) suspended in diethyl ether (50 ml) at −40° C. under nitrogen. The reaction is stirred at 20°–30° C. for 3 hrs and tetrahydrofuran (50 ml) is added followed by the dropwise addition of water. The organic layer is separated and the aqueous layer is extracted with ethyl acetate. The combined organic extracts are dried over magnesium sulfate and evaporated. The residue is subjected to chromatography on silica gel using ethyl acetate-benzene (1:4). The appropriate eluates are evaporated to give the title compound. The latter compound is dissolved in diethyl ether and anhydrous hydrogen chloride is bubbled into the solution. The precipitate is collected and triturated with acetone to obtain the hydrochloride salt of the title compound, mp 270° C. (dec).

In the same manner but replacing (6a,15b-trans)-13-chloro-1,3,4,6,6a,10,11,15b-octahydro-5H-benzo[6,7-]cyclohepta[1,2,3,-de]pyrido[2,1-a]isoquinoline-5-one with an equivalent amount of (6a,15b-cis)-13-chloro-1,3,4,6,6a,10,11,15b-octahydro-5H-benzo[6,7]cyclohepta[1,2,3-de]pyrido[2,1-a]isoquinolin-5-one (described in Example 7), (6a,15b-cis)-13-chloro-(5-hydroxyl, 15b-H-trans)-5-isopropyl-1,4,5,6,6a,10,11,15b-octahydro-5H-benzo[6,7]-cyclohepta[1,2,3-de]pyrido[2,1-a]isoquinolin-5-ol is obtained.

EXAMPLE 9

(6a,15b-trans)-(5-hydroxyl, 15b-H-trans)-13-Chloro-5-cyclohexyl-1,4,5,6,6a,10,11,15b-octahydro-5H-benzo[6,7]cyclohepta[1,2,3-de]pyrido-[2,1-a]isoquinolin-5-ol; 1a (R=cyclohexyl)

To a hexane solution of cyclohexyl lithium (2.25 M), (6a,15b-trans)-13-chloro-1,3,4,6,6a,10,11,15b-octahydro-5H-benzo[6,7]cyclohepta[1,2,3-de]pyrido[2,1-a]isoquinoline-5-one (5,8 g, described in Example 7) dissolved in 100 ml of benzene is added dropwise with stirring and cooling. After stirring at room temperature for 2.5 hours, the reaction mixture is decomposed with water. The organic layer is separated, dried over magnesium sulfate and concentrated to give the title compound. In the same manner but replacing the starting trans isomer with the cis isomer (described in Example 7), (6a, 15b-cis)-(5-hydroxy, 15b-H-trans)-13-chloro-5-cyclohexyl-1,4,5,6,6a,10,11,15b-octahydro-5H-benzo[6,7]cyclohepta[1,2,3-de]pyrido[2,1-a]isoquinolin-5-ol is obtained.

The procedure of Examples 8 or 9 is used to prepare other 5-substituted derivatives of 13-chloro-1,4,5,6,6a,10,11,15b-octahydro-5H-benzo[6,7]cyclohepta[1,2,3-de]pyrido[2,1-a]isoquinolin-5-ol, compounds of formula 1 in which R is as defined herein. An equivalent amount of the appropriate Grignard reagent in the case of the procedure of Example 8, or the appropriate lithium derivative, in the case of the procedure of Example 9, is used, instead of isopropyl magnesium chloride or cyclohexyl lithium, respectively. Examples of such 5-substituted compounds prepared in this manner, are listed in Table 1 together with the Grignard or lithium derivative that is used in the Example. In these examples the starting material of formula 2 is either the trans or cis isomer described in Example 7.

TABLE 1

| Ex. | Grignard reagent or lithium derivative, starting material | Product: [(prefix listed below)-13-chloro-(5-hydroxy, 15b-H-trans)-1,4,5,6,6a,10,11,15b-octahydro-3H-benzo[6,7]cyclohepta-[1,2,3-de]pyrido[2,1-a]isoquinolin-5-ol] Prefix |
|---|---|---|
| 10 | CH₃MgBr | 5-methyl-(6a,15b-trans) |
| 11 | C₅H₁₁MgI | 5-pentyl-(6a,15b-trans) |
| 12 | C₂H₅Li | 5-ethyl-(6a,15b-cis) |
| 13 | t-C₄H₉Li | 5-t-butyl-(6a,15b-trans) |
| 14 | (CH₂)₃ CHMgBr | 5-cyclobutyl-(6a,15b-trans) |
| 15 | (CH₂)₄ CHLi | 5-cyclopentyl-(6a,15b-cis) |

We claim:

1. A compound of formula 1

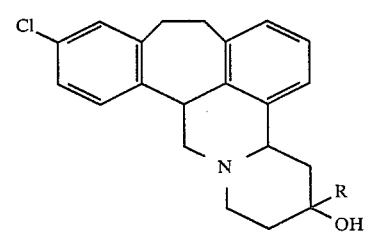

(1)

in which R is lower alkyl selected from the group consisting of straight chain alkyl having up to six carbon atoms and branched chain alkyl having up to four carbon atoms or R is cycloalkyl having 3–6 carbon atoms, or a pharmaceutically acceptable acid addition salt thereof.

2. A compound of formula 1a

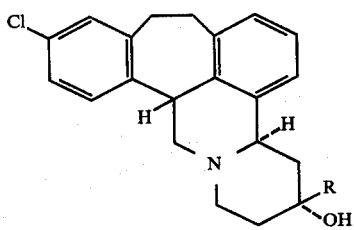

(1a)

in which R is lower alkyl selected from the group consisting of straight chain alkyl having up to six carbon atoms and branched chain alkyl having up to four carbon atoms or R is cycloalkyl having 3–6 carbon atoms, or a pharmaceutically acceptable acid addition salt thereof.

3. A compound as claimed in claim 2, wherein R is lower alkyl, or a pharmaceutically acceptable acid addition salt thereof.

4. (6a, 15b-trans)-(5-Hydroxyl, 15b-H-trans)-13-chloro-5-isopropyl-1,4,5,6,6a,10,11,15b-octahydro-5H-benzo[6,7]cyclohepta[1,2,3-de]pyrido[2,1-a]isoquinolin-5-ol, as claimed in claim 2.

5. A pharmaceutical composition for producing neuroleptic effects in a mammal comprising an effective neuroleptic amount of a compound of claim 1, or a pharmaceutically acceptable salt thereof, and a pharmaceutically acceptable carrier.

6. A pharmaceutical composition as claimed in claim 5, wherein said compound is the compound of formula 1 in which R is isopropyl.

7. A method of producing neuroleptic effects in a mammal which comprises administering to said mammal an effective neuroleptic amount of a compound of claim 1, or a pharmaceutically acceptable salt thereof.

8. A method as claimed in claim 7, wherein said compound is the compound of formula 1 in which R is isopropyl.

* * * * *